United States Patent [19]
Larson et al.

[11] Patent Number: 5,891,110
[45] Date of Patent: Apr. 6, 1999

[54] OVER-THE-WIRE CATHETER WITH IMPROVED TRACKABILITY

[75] Inventors: Christopher R. Larson, St. Paul; Brook Q. Ren, Champlin; Tim Stivland, Plymouth; Mirna A. Slayhi, Minneapolis, all of Minn.

[73] Assignee: SciMed Life Systems, Inc., Maple Grove, Minn.

[21] Appl. No.: 950,864

[22] Filed: Oct. 15, 1997

[51] Int. Cl.⁶ ............................................. A61M 25/00
[52] U.S. Cl. ........................................ 604/280; 604/282
[58] Field of Search .................................. 604/280, 282, 604/264, 51, 95, 96; 606/192–194

[56] References Cited

U.S. PATENT DOCUMENTS

| | | | |
|---|---|---|---|
| Re. 33,166 | 2/1990 | Samson | 606/194 |
| 3,911,927 | 10/1975 | Rich et al. | 128/349 R |
| 4,085,185 | 4/1978 | Adair | 264/248 |
| 4,195,637 | 4/1980 | Gruntzig et al. | 128/348 |
| 4,249,536 | 2/1981 | Vega | 128/349 B |
| 4,251,305 | 2/1981 | Becker et al. | 156/86 |
| 4,307,722 | 12/1981 | Evans | 128/344 |
| 4,323,071 | 4/1982 | Simpson et al. | 128/343 |
| 4,385,635 | 5/1983 | Ruiz | 128/658 |
| 4,413,989 | 11/1983 | Schjeldahl et al. | 604/96 |
| 4,425,919 | 1/1984 | Alston, Jr. et al. | 128/658 |
| 4,531,512 | 7/1985 | Wolvek et al. | 128/1 D |
| 4,531,943 | 7/1985 | VanTassel et al. | 604/280 |
| 4,540,404 | 9/1985 | Wolvek | 604/96 |
| 4,551,292 | 11/1985 | Fletcher et al. | 264/139 |
| 4,588,399 | 5/1986 | Nebergall et al. | 604/280 |
| 4,596,563 | 6/1986 | Pande | 604/264 |
| 4,636,272 | 1/1987 | Riggs | 156/158 |
| 4,636,346 | 1/1987 | Gold et al. | 264/139 |
| 4,676,229 | 6/1987 | Krasmicki et al. | 128/4 |
| 4,706,670 | 11/1987 | Andersen e tal. | 128/344 |
| 4,739,768 | 4/1988 | Engelson | 128/658 |
| 4,748,982 | 6/1988 | Horzewski et al. | 128/344 |
| 4,753,765 | 6/1988 | Pande | 264/149 |
| 4,759,748 | 7/1988 | Reed | 604/95 |
| 4,764,324 | 8/1988 | Burnham | 264/103 |
| 4,782,834 | 11/1988 | Maguire et al. | 128/344 |
| 4,808,164 | 2/1989 | Hess | 604/95 |
| 4,817,613 | 4/1989 | Jaraczewski et al. | 128/658 |
| 4,819,751 | 4/1989 | Shimada et al. | 128/344 |
| 4,820,349 | 4/1989 | Saab | 128/344 |
| 4,863,442 | 9/1989 | DeMello et al. | 604/282 |
| 4,884,573 | 12/1989 | Wijay et al. | 128/344 |
| 4,886,506 | 12/1989 | Lovgren et al. | 604/280 |
| 4,898,896 | 2/1990 | Maj et al. | 528/323 |
| 4,906,244 | 3/1990 | Pinchuk et al. | 606/194 |

(List continued on next page.)

FOREIGN PATENT DOCUMENTS

| | | |
|---|---|---|
| 0 171 884 A1 | 9/1986 | European Pat. Off. |
| 0 448 886 A1 | 10/1991 | European Pat. Off. |
| 0 452 595 A1 | 10/1991 | European Pat. Off. |
| 0 237 564 B1 | 12/1991 | European Pat. Off. |
| 0 594 201 A2 | 4/1994 | European Pat. Off. |
| 0 688 576 A1 | 12/1995 | European Pat. Off. |
| 0 452 901 B1 | 1/1996 | European Pat. Off. |
| WO 93/17750 | 9/1993 | WIPO |
| WO 94/01160 | 1/1994 | WIPO |

OTHER PUBLICATIONS

*Plastics Digest*, Edition 15, vol. 2, 1994, pp. 2–314.
Kohan, *Nylon Plastics Handbook*, Hanser/Gardner Publications, Inc., Cincinnati, Ohio, Copyright 1995, pp. 378–387.

*Primary Examiner*—John D. Yasko
*Attorney, Agent, or Firm*—Crompton, Seager & Tufte, LLC

[57] ABSTRACT

A catheter is disclosed which includes an over-the-wire type balloon catheter with a guide wire wherein the catheter includes a polyethylene inner tube and an outer tube having a relatively stiff proximal outer section, a midshaft section of lesser stiffness, and a tapering distal outer section of the least stiffness. An inflatable balloon is connected to the distal ends of the inner tube and the outer tube. The guide wire may be removed from and inserted into the guide wire lumen at either end of the catheter.

21 Claims, 1 Drawing Sheet

U.S. PATENT DOCUMENTS

| | | | |
|---|---|---|---|
| 4,921,483 | 5/1990 | Wijay et al. | 604/96 |
| 4,943,278 | 7/1990 | Euteneuer et al. | 604/96 |
| 4,955,377 | 9/1990 | Lennox et al. | 128/401 |
| 4,960,410 | 10/1990 | Pinchuk | 604/96 |
| 4,964,409 | 10/1990 | Tremulis | 128/657 |
| 4,964,853 | 10/1990 | Sugiyama et al. | 604/96 |
| 4,976,720 | 12/1990 | Machold et al. | 606/194 |
| 4,994,018 | 2/1991 | Saper | 600/18 |
| 5,002,559 | 3/1991 | Tower | 606/194 |
| 5,047,045 | 9/1991 | Arney et al. | 606/194 |
| 5,050,606 | 9/1991 | Tremulis | 128/637 |
| 5,078,702 | 1/1992 | Pomeranz | 604/280 |
| 5,078,727 | 1/1992 | Hannam et al. | 606/194 |
| 5,093,546 | 3/1992 | Matsumiya et al. | 219/10.41 |
| 5,100,381 | 3/1992 | Burns | 604/96 |
| 5,120,308 | 6/1992 | Hess | 604/95 |
| 5,122,125 | 6/1992 | Deuss | 604/282 |
| 5,139,496 | 8/1992 | Hed | 606/23 |
| 5,143,093 | 9/1992 | Sahota | 128/898 |
| 5,147,377 | 9/1992 | Sahota | 606/194 |
| 5,154,725 | 10/1992 | Leopold | 606/194 |
| 5,156,594 | 10/1992 | Keith | 604/96 |
| 5,156,612 | 10/1992 | Pinchuk et al. | 606/194 |
| 5,158,548 | 10/1992 | Lau et al. | 604/96 |
| 5,159,937 | 11/1992 | Tremulis | 128/772 |
| 5,171,230 | 12/1992 | Eland et al. | 604/250 |
| 5,176,637 | 1/1993 | Sagae | 604/96 |
| 5,180,585 | 1/1993 | Jacobson et al. | 424/405 |
| 5,209,728 | 5/1993 | Kraus et al. | 604/96 |
| 5,213,574 | 5/1993 | Tucker | 604/93 |
| 5,221,270 | 6/1993 | Parker | 604/282 |
| 5,226,888 | 7/1993 | Arney | 604/96 |
| 5,234,416 | 8/1993 | Macaulay et al. | 604/282 |
| 5,240,537 | 8/1993 | Bodicky | 156/244.13 |
| 5,254,091 | 10/1993 | Aliahmad et al. | 604/96 |
| 5,256,144 | 10/1993 | Kraus et al. | 604/96 |
| 5,258,160 | 11/1993 | Utsumi et al. | 264/558 |
| 5,259,839 | 11/1993 | Burns | 604/99 |
| 5,270,086 | 12/1993 | Hamlin | 428/35.2 |
| 5,279,561 | 1/1994 | Roucher et al. | 604/96 |
| 5,279,562 | 1/1994 | Sirhan et al. | 604/96 |
| 5,304,134 | 4/1994 | Kraus et al. | 604/96 |
| 5,304,198 | 4/1994 | Samson | 606/194 |
| 5,316,706 | 5/1994 | Muni et al. | 264/25 |
| 5,318,032 | 6/1994 | Lonsbury et al. | 128/658 |
| 5,318,527 | 6/1994 | Hyde et al. | 604/95 |
| 5,318,532 | 6/1994 | Frassica | 604/96 |
| 5,324,259 | 6/1994 | Taylor et al. | 604/96 |
| 5,324,263 | 6/1994 | Kraus et al. | 604/96 |
| 5,328,468 | 7/1994 | Kaneko et al. | 604/96 |
| 5,334,148 | 8/1994 | Martin | 604/96 |
| 5,334,168 | 8/1994 | Hemmer | 604/281 |
| 5,335,410 | 8/1994 | Burnham | 29/452 |
| 5,342,386 | 8/1994 | Trotta | 606/194 |
| 5,344,400 | 9/1994 | Kaneko et al. | 604/96 |
| 5,346,505 | 9/1994 | Leopold | 606/194 |
| 5,370,615 | 12/1994 | Johnson | 604/96 |
| 5,370,655 | 12/1994 | Burns | 606/194 |
| 5,387,193 | 2/1995 | Miraki | 604/96 |
| 5,389,087 | 2/1995 | Miraki | 604/247 |
| 5,397,306 | 3/1995 | Nobuyoshi et al. | 604/96 |
| 5,399,164 | 3/1995 | Snoke et al. | 604/95 |
| 5,403,292 | 4/1995 | Ju | 604/282 |
| 5,405,338 | 4/1995 | Kranys | 604/282 |
| 5,411,477 | 5/1995 | Saab | 604/96 |
| 5,423,754 | 6/1995 | Cornelius et al. | 604/103 |
| 5,425,709 | 6/1995 | Gambale | 604/96 |
| 5,425,712 | 6/1995 | Goodin | 604/96 |
| 5,454,795 | 10/1995 | Samson | 604/282 |
| 5,458,613 | 10/1995 | Gharibadeh et al. | 606/194 |
| 5,470,322 | 11/1995 | Horzewski et al. | 604/280 |
| 5,480,383 | 1/1996 | Bagnoisan et al. | 604/96 |
| 5,496,271 | 3/1996 | Burton et al. | 604/54 |
| 5,496,294 | 3/1996 | Hergenrother et al. | 604/282 |
| 5,503,263 | 4/1996 | Watanabe | 198/442 |
| 5,509,910 | 4/1996 | Lunn | 604/282 |
| 5,531,715 | 7/1996 | Engelson et al. | 604/265 |
| 5,538,513 | 7/1996 | Okajima | 604/282 |
| 5,540,236 | 7/1996 | Ginn | 128/772 |
| 5,542,924 | 8/1996 | Snoke et al. | 604/95 |
| 5,542,937 | 8/1996 | Chee et al. | 604/280 |
| 5,549,552 | 8/1996 | Peters et al. | 604/96 |
| 5,549,556 | 8/1996 | Ndondo-Lay et al. | 604/102 |
| 5,554,121 | 9/1996 | Ainsoworth et al. | 604/96 |
| 5,554,139 | 9/1996 | Okajima | 604/282 |
| 5,569,218 | 10/1996 | Berg | 604/282 |
| 5,605,543 | 2/1997 | Swanson | 604/96 |
| 5,643,209 | 7/1997 | Fugoso et al. | 604/96 |
| 5,645,528 | 7/1997 | Thome | 604/96 |
| 5,716,373 | 2/1998 | Wolvek et al. | 606/194 |
| 5,725,513 | 3/1998 | Ju et al. | 604/280 |
| 5,728,063 | 3/1998 | Preissman et al. | 604/96 |
| B1 4,323,071 | 5/1990 | Simpson et al. | 128/343 |

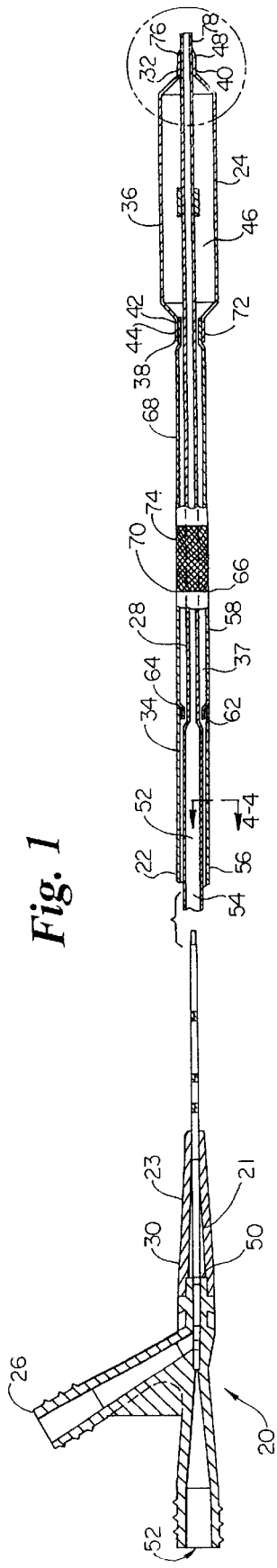
Fig. 1
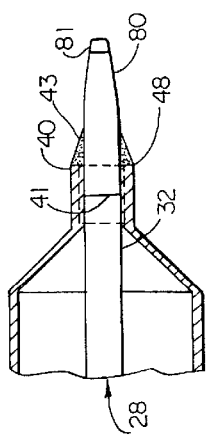
Fig. 3
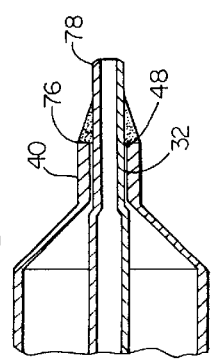
Fig. 2
Fig. 4

OVER-THE-WIRE CATHETER WITH IMPROVED TRACKABILITY

TECHNICAL FIELD

This invention relates to the field of intravascular medical devices used in combination with guide members. More specifically, the present invention relates to intravascular balloon dilation catheters for use in combination with guide wires, wherein the outer tube member of the catheter incorporates a relatively stiff proximal outer section, a midshaft portion of lesser stiffness, and a tapering distal outer section of the least stiffness for improved pushability, trackability and crossability.

BACKGROUND OF THE INVENTION

Intravascular diseases are commonly treated by relatively non-invasive techniques such as percutaneous transluminal angioplasty (PTA) and percutaneous transluminal coronary angioplasty (PTCA). These therapeutic techniques are well known in the art and typically involve the use of a balloon catheter with a guide wire, possibly in combination with other intravascular devices. A typical balloon catheter has an elongate shaft with a balloon attached proximate the distal end and a manifold attached to the proximal end.

In use, the balloon catheter is advanced over the guide wire such that the balloon is positioned adjacent a restriction in a diseased vessel. The balloon is then inflated and the restriction in the vessel is opened.

There are two basic types of balloon catheters used in combination with a guide wire, namely, over-the-wire (OTW) catheters and single-operator-exchange (SOE) catheters. The construction and use of both OTW catheters and SOE catheters are well-known in the art. An example of an OTW catheter may be found in commonly-assigned U.S. Pat. No. 5,047,045 to Arney et al. An example of an SOE balloon catheter is disclosed in commonly-assigned U.S. Pat. No. 5,156,594 to Keith.

PTA and PTCA catheters are preferably designed to optimize pushability, trackability and crossability. Pushability is defined as the ability to transmit force from the proximal end of the catheter to the distal end of the catheter. Trackability is defined as the ability to navigate tortuous vasculature. Crossability is defined as the ability to navigate the balloon catheter across narrow restrictions in the vasculature.

OTW balloon catheters may be classified into two groups. The first group comprising multi-lumen OTW balloon catheters, and the second group comprising coaxial OTW balloon catheters. Multi-lumen OTW catheters typically include a single extrusion shaft having two side-by-side longitudinally extending lumens, namely an inflation lumen and a guide wire lumen. By contrast, a coaxial OTW catheter typically includes two separate tubes, namely an inner tube and a coaxially disposed outer tube. The inner tube defines a guide wire lumen and an annular inflation lumen is defined between the inner tube and the coaxially disposed outer tube.

Prior art coaxial OTW-type balloon catheters have attempted to maximize pushability by incorporating a stainless steel outer tube on the proximal shaft portion (also referred to as a hypotube) and a polymeric distal shaft portion. Hypotubing is, however, prone to kinking. Coaxial OTW-type balloon catheters can also incorporate a polymer shaft or a reinforced polymer shaft as a proximal shaft portion (e.g. composite) as a compromise between maximizing pushability and minimizing the probability of kinking in the proximal shaft portion.

The trackability of a particular catheter design is analyzed in terms of the trackability of the distal portion of the catheter, as this portion must track the guidewire through small tortious vessels to reach the stenosed area to be treated. A more flexible distal portion has been found to improve trackability. Further, in transitioning from a stiff proximal segment or portion of the catheter shaft to a more flexible distal portion of the catheter shaft, it has been found that kinking readily occurs at the joint between the two shaft segments of differing flexibility. The increased flexibility of the distal section also makes this portion of the catheter less able to be pushed from the proximal end of the catheter.

Pushability without kinking, trackability and crossability are all features desirable in a catheter design. However, factors which improve one feature, such as pushability, can have a detrimental impact on trackability and vice versa. There is an unmet need for a coaxial over-the-wire type balloon catheter which incorporates features that provide improved pushability without kinking and an improved trackability in order to cross tight lesions in tortious anatomy.

SUMMARY OF THE INVENTION

The present invention may be described as a medical system including an over-the-wire type balloon catheter and a guide wire wherein the catheter includes a polyethylene inner tube and an outer tube having a relatively stiff proximal outer section, a midshaft section of lesser stiffness, and a tapering distal outer section of the least stiffness. Such an arrangement of progressively more flexible materials as the catheter proceeds distally provides an optimal level of pushability and trackability to navigate tortuous vasculature.

The inner tube defines a guide wire lumen and is coaxially disposed inside the outer tube to define an annular inflation lumen therebetween. An inflatable balloon has a distal end connected to the inner tube proximate distal end, and a proximal end connected to the outer tube proximate the outer tube distal end. The guide wire has a maximum outside diameter which is less than the minimum inside diameter of the guide wire lumen such that the guide wire may be removed from or inserted into the guide wire lumen at either end of the catheter.

In one embodiment, a distal tip is formed at the distal end of the inner tube wherein a distal portion of the inner tube extends distally beyond the site where the distal waist of the balloon is bonded to the distal end of the inner tube. Within this bonding region, the distal end of the inner tube distally tapers to a smaller outer diameter.

In another embodiment, a tapering distal tip of lesser stiffness is heat welded to the distal end of the inner at an axial location under the balloon's distal waist. The balloon is then adhesively bonded to both the distal end or portion of the inner tube covered by the distal waist and the proximal portion of the distal tip which is also under the distal waist of the balloon. This forms a secure joint.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 1 is a cross-sectional view of a catheter showing a preferred embodiment of the present invention;

FIG. 2 is a partial cross-sectional view of a preferred embodiment distal tip area of the catheter of FIG. 1, illustrating the tip formed from the inner;

FIG. 3 is a partial cross-sectional view of a second preferred embodiment of distal tip area of the catheter of FIG. 1, illustrating the transition between the stiffer distal end of the inner tube and the more flexible distal tip; and FIG. 4 is a cross section view of FIG. 1 taken along line 4—4;

DETAILED DESCRIPTION OF THE PREFERRED EMBODIMENTS

The following detailed description should be read with reference to the drawings in which like elements in different drawings are numbered identically. The drawings, which are not necessarily to scale, depict selected embodiments and are not intended to limit the scope of the invention.

Examples of constructions, materials, dimensions and manufacturing processes are provided for selected elements. All other elements employ that which is known to those skilled in the field of the invention. Those skilled in the art will recognize that many of the examples provided have suitable alternatives which may also be utilized.

Referring now to the drawings, FIG. 1 is a cross-sectional view of an over-the-wire balloon catheter showing a preferred embodiment of the present invention. The balloon catheter 20 includes a shaft assembly 22 and a balloon assembly 24 connected proximate its distal end. A conventional OTW-type manifold assembly 26 is connected to the proximal end of the shaft assembly 22. The shaft assembly 22 includes an inner tube 28 having a proximal end 30 and a distal end 32. The proximal end of the shaft assembly 21 extends into a manifold assembly 26 adhesively bonded to the shaft assembly 22. A polyurethane strain relief 23 is snap-fit to the manifold assembly 26, and the shaft assembly 22 extends into the manifold assembly 26 through the polyurethane strain relief 23. An outer tube 34 is coaxially disposed about the inner tube 28 to define an annular inflation lumen 37.

The balloon assembly 24 includes a balloon body portion 36 with a proximal balloon waist 38 and a distal balloon waist 40. The proximal balloon waist 38 is connected to the outer tube 42 near its distal end by means of an adhesive 44. The distal balloon waist 40 is connected to the inner tube 28 near its distal end 32 by means of an adhesive bond 48 such that the interior of the balloon 46 is in fluid communication with the annular inflation lumen 37.

A radiopaque marker band 50 is adhesively secured with cyanoacrylate to the inner tube 28 at a point underneath the balloon body 36. Alternatively, the marker band may be swaged onto the outer surface of the inner. The inner tube 28 defines a guide wire lumen 54 which provides a passage for a guide wire (not shown). The outer tube 34 defines an annular inflation lumen 37 which is in fluid communication with the interior of the balloon 46.

As previously stated, the catheter of the present invention includes an outer tube having a relatively stiff proximal outer section, a mid-shaft section of lesser stiffness, and a tapering distal outer section of the least stiffness. The progressive arrangement of more flexible materials as the catheter proceeds distally provides an optimal level of pushability and trackability to navigate tortious vasculature. The flexibility of the segments of the outer tubular member were tested utilizing a Gurley bending resistance tester, Part No. 4171-DT, as manufactured by Precision Instruments, Troy, New York. The apparatus consists of a balanced pendulum or pointer which is centerpivoted and can be weighted at three points below its center. The pointer moves freely in both the left and right directions. A sample of specific size is attached to a clamp, which in turn, is located in one of several positions on a motorized arm which also moves left and right. During the test, the sample is moved against the top edge of the vane, moving the pendulum until a sample bends and releases it. The test is run in two steps, first to the left and then to the right. The scale reading is measured in each direction and the results are averaged. The instrument provides a relative flexibility measurement between the components of the outer tubular member as detailed below to achieve improved trackability and pushability.

The outer tube 34 has a relatively stiff, proximal outer section 56 with a proximal end 60 and a distal end 62. The proximal outer tube may be made of nylon, a polyamide, such as DURETHAN available from Bayer, a DURETHAN braid or polyetheretherketone (PEEK) braid. The preferred embodiment of PEEK braid is a variable PIC tube, wherein said PIC varies from about 30 to 100 PIC to give varying flexibility over the length of the proximal outer tube. The PIC preferably varies from about 50 to about 80. The braiding material in the PEEK or DURETHAN (polymer) braid may be made from stainless steel, or Nitinol (nickel titanium alloy). This proximal outer section 56 will have an outside diameter ranging from 0.040 inches to 0.045 inches with a wall thickness ranging from 0.0028 inches to 0.0044 inches. The proximal outer section has a preferred Gurley value of about 700 to about 1300 over its length. A preferred range is about 800 to about 1200. FIG. 4 illustrates a cross section view of the proximal outer section having PEEK braid material as taken along 4—4 of FIG. 1. The PEEK braid includes an inner layer, a braid layer and an outer layer.

A midshaft section 58 with a proximal end 64 and a distal end 66 extends distally from the distal end of the proximal outer section 62. The midshaft section 58 has a stiffness less than that of the proximal outer section 56. The midshaft section 58 is preferably made from a polyamide, such as CRISTAMID available from Elf Atochem, having a durometer of about 81D. A preferred Gurley value for the midsection is about 350 to about 500, with a range of 400 to 450 preferred. This midshaft section 58 will have an outside diameter ranging from 0.040 inches to 0.045 inches with a wall thickness ranging from 0.0028 inches to 0.0044 inches.

The distal end of the proximal outer section 62 is joined to the proximal end of the midshaft section 64 with a urethane adhesive bond or a thermal weld. A distal outer section 68 having a proximal end 70 and a distal end 72 extends distally from the distal end of the midshaft section 66 to the distal end of the outer tube 44. This distal outer section 68 is more flexible or has less stiffness than both the proximal outer section 56 and the midshaft section 58. The outer diameter of the distal outer section 68 will taper from about 0.045 inches at the proximal end 70 to 0.030 inches at the distal end 72. This distal outer section 68 is made of polyether block amide (PEBAX) with a durometer of 70D. The tapered distal outer section preferably has a Gurley value of about 70 to about 90 at its proximal end and about 15 to about 40 at its distal end. Thus, the distal end of the distal outer section 72 will exhibit less stiffness than the proximal end of the distal outer section 70. The distal end of the midshaft section 66 is joined to the proximal end of the distal outer section 70 with a urethane adhesive bond or a thermal weld.

A Nitinol braid insert 74 with a length of about 1.0" is placed within the proximal end of the distal outer section 70 to provide strain relief and reduce kinkability at the midshaft/distal outer section junction. This Nitinol braid 74 has a 0.001"×0.005" ribbon.

The inner tube 28 is made of polyethylene such as Marlex HDPE. At the proximal end of the inner tube 30, the inner tube 28 has an outside diameter ranging from 0.024 inches to 0.026 inches and preferably about 0.025 inches, with the inner tube 28 having an inside diameter ranging from 0.018 inches to 0.0195 inches for a 0.014 inch guide wire for which this lumen is designed to be compatible with. The inner tube 28 has a wall thickness ranging from 0.0026 inches to 0.004 inches and preferably about 0.0032 inches. The outside diameter to wall thickness ratio must be sufficiently small to minimize the propensity of kinking.

As the inner tube 28 extends distally through the junction area between the distal end of the proximal outer section 62 and the proximal end of the midshaft section 64 of the outer tube 28, both the inner and outer diameters of the inner tube 28 will taper from wider diameters to narrower diameters. Likewise, at the distal end of the inner tube 32, both the inner and outer diameters of the inner tube 28 will once again taper from wider diameters to narrower diameters as the tube extends distally.

As illustrated in FIG. 2, in one preferred embodiment, a distal tip 76 is formed on the distal end of the inner tube 32 where the inner tube 28 distally tapers from a larger outer diameter to a smaller outer diameter. The distal balloon waist 40 is attached to the distal tip 76 through a urethane adhesive bond at a bonding area. The area just distal of the distal waist bond is backfilled with adhesive 43 to provide a smooth transition. The adhesive coating provides for improved adhesion between dissimilar substrates.

The proximal catheter shaft portion is preferably about 35 to 45 inches in length with a preferred length of 42 inches. The midshaft section is preferably about 1 to about 3 inches in length with a preferred length of 2 inches. The distal outer section having the most flexibility is preferably about 8 to about 12 inches in length with a preferred length of about 10 inches.

In another preferred embodiment, as shown in FIG. 3, a polyethylene distal tip 80 of durometer between about 45D and 65D, preferably about 55D is heat welded or bonded to the distal end of the inner tube 32 with a durometer of about 63–65D, and the distal balloon waist 40 of the balloon is adhesively bonded to both the inner and the tip extending therefrom. As shown in FIG. 3, the joint 41 between the inner and the tip is located under the distal waist of the balloon. The outer diameter of the polyethylene distal tip 80 distally tapers from a larger outer diameter to a smaller outer diameter.

In another preferred embodiment, incorporating a soft tip as described above, the last ½ to 1 mm of the tip at its distal end is made of a different material from the tip material to form a tip extension. In particular, the last ½ to 1 mm is made from a material which is more durable relative to the softer tip material. In particular, the more durable material will resist deforming or tearing when in use, such as tracking tortuous anatomy or through a placed stent. For example, this last ½ to 1 mm may be manufactured from Marlex high density polyethylene having a 63D durometer which improves the integrity of the tip portion at its distal most end 81.

Having thus described the preferred embodiments of the present invention, those of skill in the art will readily appreciate that yet other embodiments may be made and used within the scope of the claims hereto attached.

What is claimed:

1. An over-the-wire type balloon catheter, comprising:
   a. an outer tube having a proximal end and a distal end including a proximal outer section extending distally a predefined distance from the proximal end of the outer tube, wherein said proximal outer section has a proximal end, a distal end, and a first stiffness, said outer tube further including a midshaft section extending distally a predefined distance from the distal end of said proximal outer section, wherein said midshaft section has a proximal end, a distal end, and a second stiffness less than said first stiffness of the proximal outer section, wherein said midshaft section and said proximal outer sections are connected at a first junction, and a distal outer section of the outer tube extending distally from the distal end of said midshaft section to the distal end of said outer tube, wherein said distal outer section has a proximal end, a distal end, and a third stiffness less than said second stiffness of the midshaft section, wherein said distal outer section and said midshaft sections are connected at a second junction, said distal outer section tapering from a wider diameter at the proximal end to a narrower diameter at the distal end such that the proximal end has a greater stiffness and distal end has a lesser stiffness; and
   b. a braided insert placed within the lumen of the proximal end of said distal outer section, extending distally from said second junction, said braid section providing strain relief at said second junction;
   c. an elongate inner tube having a proximal end and a distal end with a lumen extending therethrough coaxially disposed within the lumen of the outer tube to form an inflation lumen therebetween; and
   d. an inflatable balloon sealably connected proximate the distal end of the outer tube, and proximate the distal end of the inner tube, the interior of the balloon being in fluid communication with the inflation lumen.

2. A catheter as in claim 1 wherein said inner tube tapers from a greater diameter to a lesser diameter as it extends distally through the first junction.

3. A catheter as in claim 1 wherein the material of said proximal outer section is selected from the group consisting of polyetheretherketone braid, nylon, polyamide and polyamide braid.

4. A catheter as in claim 3 wherein said proximal outer section is made of said polyetheretherketone braid having a braid made from a material selected from the group consisting of stainless steel and nickel titanium alloy.

5. A catheter as in claim 3 wherein said braid is a variable PIC tube, wherein said PIC varies from 30 to 100 PIC.

6. A catheter as in claim 3 wherein said proximal outer section has a length of approximately 42 inches.

7. A catheter as in claim 3 wherein said proximal outer section has a Gurley value of about 700 to about 1300.

8. A catheter as in claim 1 wherein said midshaft section is made of polyamide.

9. A catheter as in claim 8 wherein said midshaft section has a length of approximately 2 inches.

10. A catheter as in claim 8 wherein said midshaft section has a Gurley value of about 400 to about 450.

11. A catheter as in claim 8 wherein said distal outer section is made of polyether block amide.

12. A catheter as in claim 11 wherein said distal outer section has a Gurley value ranging from about 15 to about 100.

13. A catheter as in claim 11 wherein said distal outer section has a length of approximately 10 inches.

14. A catheter as in claim 1 wherein said braid component is made of nickel titanium alloy.

15. A catheter as in claim 14 wherein said braid component further comprises a braid about 1.0" long with a 0.001"×0.005" ribbon.

16. A catheter as in claim 1 wherein said first junction further comprises a urethane bonding material distributed between the proximal end of the midshaft section and the distal end of the proximal outer section.

17. A catheter as in claim 1 wherein said second junction further comprises a thermal weld between the distal end of the midshaft section and the proximal end of the distal outer section.

18. A catheter as in claim 1 wherein a marker band is attached to the distal portion of the inner tube enclosed by said inflatable balloon.

19. A catheter system as in claim 1 wherein a distal tip is formed on the distal end of said inner tube where said inner tube distally tapers from a larger outer diameter to a smaller outer diameter.

20. A catheter as in claim 1 wherein a distal tip having a durometer of about 45D to about 65D is bonded to both the distal end of said inner tube with durometer of about 63–65D, and the distal waist of said balloon, wherein said distal tip tapers distally from a larger outer diameter to a smaller outer diameter and extends distally of said balloon.

21. A catheter as in claim 20, further comprising a distal tip extension manufactured from a more durable material than the distal tip.

* * * * *

UNITED STATES PATENT AND TRADEMARK OFFICE
CERTIFICATE OF CORRECTION

PATENT NO. : 5,891,110
DATED : April 6, 1999
INVENTOR(S) : Larson et al.

It is certified that error appears in the above-identified patent and that said Letters Patent is hereby corrected as shown below:

Column 6, line 61, change "claim 8" to --claim 1--.

Signed and Sealed this

Twentieth Day of July, 1999

Attest:

Attesting Officer

Q. TODD DICKINSON

Acting Commissioner of Patents and Trademarks